United States Patent
Cook et al.

(10) Patent No.: US 7,531,651 B2
(45) Date of Patent: May 12, 2009

(54) BENZENESULPHONATE SALT OF A MORPHOLINE UREA DERIVATIVE FOR USE AS A CCR-3 ANTAGONIST IN THE TREATMENT OF INFLAMMATORY CONDITIONS

(75) Inventors: John Spencer Cook, Stevenage (GB); Robert Philip Landon, Stevenage (GB); Andrew John Walker, Stevenage (GB); Mark Wilkinson, Stevenage (GB)

(73) Assignee: Glaxo Group Limited, Greenford, Middlesex (GB)

(*) Notice: Subject to any disclaimer, the term of this patent is extended or adjusted under 35 U.S.C. 154(b) by 600 days.

(21) Appl. No.: 10/509,521

(22) PCT Filed: Mar. 27, 2003

(86) PCT No.: PCT/EP03/03345
§ 371 (c)(1),
(2), (4) Date: Jun. 10, 2005

(87) PCT Pub. No.: WO03/082293
PCT Pub. Date: Oct. 9, 2003

(65) Prior Publication Data
US 2006/0089497 A1    Apr. 27, 2006

(30) Foreign Application Priority Data
Mar. 28, 2002 (GB) .................................. 0207432.6

(51) Int. Cl.
C07D 265/30    (2006.01)
C07D 295/00    (2006.01)
A61K 31/535    (2006.01)

(52) U.S. Cl. .................... 544/106; 544/63; 544/98; 544/107; 544/162; 514/228.8; 514/231.2; 514/237.8; 514/239.5

(58) Field of Classification Search ............... 544/63, 544/98, 106, 107, 162; 514/228.8, 231.2, 514/237.8, 239.5
See application file for complete search history.

(56) References Cited

FOREIGN PATENT DOCUMENTS

| EP | 0760362 | 3/1997 |
|---|---|---|
| WO | WO 00/31032 | 6/2000 |
| WO | WO 02/26723 | 4/2002 |

OTHER PUBLICATIONS

Berge, Stephen M., Pharmaceutical Salts, Journal of Pharmaceutical Sciences, 66(1) (1977) 1-19.*
Gripenberg, M, Scand. J. Rheumatology, vol. 10 (2) 1981, 85-91.*
Barnes, P.J., Pharmacological Reviews, vol. 56, No. 4, p. 515-548, (2004).*
Kato et al., "Novel benzamides as selective and potent gastric prokinetic agents 2.. Synthesis and structure-activity relationships of 4-Amino-5-Chloro-2-Ethoxy-N-4-(4-Fluorobenzyl)-2-Morpholinyl Methylbenzamide Citrate (AS-4370) and related compounds," *Journal of Medicinal Chemistry* 34(2):1616-624 (Feb. 1991).
Lazareno et al., "Estimation of competitive antagonist affinity from functional inhibition curves using the Gaddum, Schild and Cheng-Prusoff equations," *Br. J. Pharmacol* 109:1110-1119 (1995).
Motegi et al., "Interaction with secretory component stimulates effector functions of human eosinophils but not of neutrophils," *Journal of Immunology* 161:4340-4346 (1998).

* cited by examiner

*Primary Examiner*—Kamal A Saeed
*Assistant Examiner*—Samantha L Shterengarts
(74) *Attorney, Agent, or Firm*—James P. Riek (57) ABSTRACT

Compounds of formula (I):

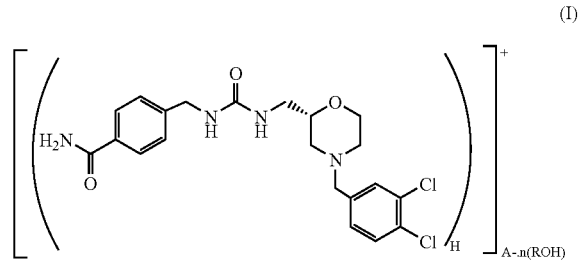

wherein $A^-$ represents the benzenesulphonate (besylate) anion;.
R represents H or $C_{1-6}$ alkyl; and
n is a number from 0.8 to 2.2 are CCR3 antagonists and are therefore indicated to be useful in therapy are described.

12 Claims, 2 Drawing Sheets

BENZENESULPHONATE SALT OF A MORPHOLINE UREA DERIVATIVE FOR USE AS A CCR-3 ANTAGONIST IN THE TREATMENT OF INFLAMMATORY CONDITIONS

CROSS-REFERENCE TO RELATED APPLICATIONS

This application is filed pursuant to 35 USC 371 as a United States National Phase Application of International Patent Application Serial No. PCT/EP03/03345 filed on 27 Mar. 2003, which claims priority from GB 0207432.6 filed on 28 Mar. 2002 in the United Kingdom.

FIELD OF THE INVENTION

This invention relates to a novel chemical compound, processes for its preparation, pharmaceutical formulations containing it, and its use in therapy.

BACKGROUND OF THE INVENTION

Co-pending International Patent Application number PCT/GB01/04530 (Glaxo Group Limited) relates to certain morpholine urea derivatives which block the migration/chemotaxis of eosinophils.

It has now surprisingly been found that a specific compound falling within formula (I) of PCT/GB01/04530 has particularly advantageous physicochemical properties, more suitable for the preparation of large scale quantities and for use in the preparation of pharmaceutical formulations. In particular, the compound is crystalline and non-hygroscopic, stable, and displays good solubility profiles.

Specifically, the crystalline nature of the compound is ideal for isolation and purification and is sufficiently stable for use in conventional pharmaceutical formulations. These advantages confer significant benefits of formulation and handling.

SUMMARY OF THE INVENTION

Thus, according to one aspect of the invention, there is provided a compound of formula (I):

(I)

wherein A⁻ represents the benzenesulphonate (besylate) anion;.

R represents H or $C_{1-6}$alkyl; and n is a number from 0.8 to 2.2.

Preferably R represents H.

Preferably n represents a number between 1.1 and 2.1, more preferably about 2.

In a preferred aspect the present invention therefore provides 4-({[({[(2S)-4-(3,4-dichlorobenzyl)morpholin-2-yl]methyl}amino)carbonyl]amino}methyl)benzamide benzenesulfonate dihydrate.

The compound 4-({[({[(2S)-4-(3,4-dichlorobenzyl)morpholin-2-yl]methyl}amino)carbonyl]amino}methyl)benzamide is disclosed in co-pending patent application PCT/GB01/04530, however the besylate salt has not previously been disclosed. We have found that the compound 4-({[({[(2S)-4-(3,4-dichlorobenzyl) morpholin-2-yl]methyl}amino)carbonyl]amino}methyl)benzamide does not readily form salts suitable for pharmaceutical use.

In a further aspect of the invention, there is provided a process for the preparation of a compound of formula (I), which process comprises the reaction of a compound of formula (IA);

(IA)

with a source of the besylate anion and a suitable $C_{1-6}$alkanol and water.

Suitable sources of the besylate anion are benzenesulphonic acid and besylate salts such as ammonium besylate. A preferred source of the besylate anion is benzenesulphonic acid.

Typically, the compound of formula (IA) is suspended in a suitable $C_{1-6}$ alkanol, suitably ethanol or iso-propyl alcohol, and water at elevated temperature, suitably a temperature in the range 35-45° C. A solution of the source of besylate anion, preferably benzene sulfonic acid, in water is added. A suitable anti solvent, suitably isopropyl acetate, is optionally added to the solution and the mixture is cooled to 0-25° C. A suitable non-polar solvent such as an aliphatic hydrocarbon, e.g cyclohexane may optionally be added. The mixture may optionally be seeded with crystals of the compound of formula (I). The mixture is maintained at a reduced temperature for a suitable period of time to allow crystallisation of the product, and isolated by filtration. Suitable seed crystals of the compound of formula (I) may be prepared by spontaneous crystallisation of a mixture of compound of formula (IA) and benzenesulphonic acid from aqueous $C_{1-6}$-alkanol mixtures at reduced temperature, suitably 0-25° C.

The compound of formula (IA) may be prepared by reacting the compound of formula (II), or a salt thereof (II)

with a compound of formula (III), or a salt thereof (III)

in the presence of a suitable amine coupling agent, such as N,N'-carbonyldiimidazole.

Typically, a compound of formula (II) in a suitable first solvent is reacted with N,N'-carbonyldiimidazole in the same solvent at reduced temperature, suitably a temperature in the range −10-20° C. over a suitable period of time, for example 5-60 minutes. Suitable solvents include tetrahydrofuran, dichloromethane, $C_{3-4}$ alkanol, isopropyl acetate, N-methylpyrrolidinone and N,N-dimethylformamide. The mixture is warmed to a suitable temperature, suitably 5-30° C. and held at this temperature for a suitable period of time, for example 10-60 minutes. A suitable solvent, suitably iso-propyl alcohol, is added at a suitable temperature, suitably 20-30° C., and held at this temperature for a suitable period of time, for example 15-60 mins. The compound of formula (III) is then added, the mixture heated to a suitable elevated temperature, for example a temperature in the range 40-65° C., and stirred for a suitable period of time, for example 60-360 minutes. The reaction is then cooled to a suitable temperature, and a suitable second solvent, for example isopropyl acetate, added, followed by a aqueous solution of a suitable acidic salt, such as potassium dihydrogen phosphate, or suitable acid such as acetic acid. The lower aqueous layer removed and the upper organic layer washed with further acid or acidic salt solution, followed by water. The organic phase is distilled at atmospheric pressure to remove the first solvent and leave a slurry or solution of the compound of formula (IA) in the second solvent. This may then be used directly to prepare the compound of formula (I), or filtered to give the compound of formula (IA).

The compound of formula (I) may also be prepared in situ by the reaction of a compound of formula (II) or a salt thereof with a compound of formula (III) or a salt thereof, followed by addition of benzene sulphonic acid, suitably an aqueous solution of benzene sulphonic acid. i.e. without isolation of the compound of formula (IA).

Accordingly, there is provided a process for the preparation of a compound of formula (I) which process comprises the reaction of a compound of formula (II) or a salt thereof with a compound of formula (III) or a salt thereof followed by the addition of benzene sulphonic acid, or an aqueous solution thereof, to provide a compound of formula (I).

Typically, a compound of formula (II) in a suitable first solvent is reacted with N,N'-carbonyldiimidazole in the same solvent at reduced temperature, suitably a temperature in the range −10-20° C. over a suitable period of time, for example 5-60 minutes. Suitable solvents include tetrahydrofuran, dichloromethane, $C_{3-4}$ alkanol, iso-propyl acetate, N-methylpyrrolidinone and N,N-dimethylformamide. The mixture is warmed to a suitable temperature, suitably 5-30° C. and held at this temperature for a suitable period of time, for example 10-60 minutes. A suitable solvent, suitably iso-propyl alcohol, is added at a suitable temperature, suitably 5-30° C., and held at this temperature for a suitable period of time, for example, 15-60 min. The compound of formula (III) is then added, the mixture heated to a suitable elevated temperature, for example a temperature in the range 40-65° C., and stirred for a suitable period of time, for example 60-360 minutes. The reaction is then cooled to a suitable temperature, and a suitable second solvent, for example iso-propyl acetate, is added, followed by a aqueous solution of a suitable acidic salt, such as potassium dihydrogen phosphate, or suitable acid such as acetic acid. The solution is clarified if necessary, the lower aqueous layer removed and the upper organic layer washed with further acid or acidic salt solution, followed by water. The organic phase is distilled at atmhospheric pressure to low volume, a suitable solvent, suitably iso-propyl alcohol, is added and the concentration step is repeated. A solution of benzenesulfonic acid in water is added at a suitable temperature, suitably 15-45° C., followed by addition of a suitable anti-solvent, suitably isopropyl acetate. The mixture may be optionally seeded with crystals of the compound of formula (I). Further anti-solvent may be added, the mixture is cooled to 0-10° C., and maintained at a reduced temperature for a suitable period. The mixture is then filtered to give the compound of formula (I).

A compound of formula (II) may be prepared by either by Reaction (a), Reaction (b), or Reaction (c).

Reaction (a). Reaction of the compound of formula (IV) with a compound of formula (V)

(IV)

(V)

wherein A is a protected amino group, suitably phthalimido, to give a compound of formula (IIAR)

(IIAR)

wherein A is as previously defined, followed by deprotection of the amino group to give a compound of formula (IIR)

(IIR)

followed by resolution of the resulting enantiomers of the compound of formula (IIR);

or;

Reaction (b). Reaction of a compound of formula (IV) as hereinbefore defined with a compound of formula (VA)

(VA)

wherein A is as hereinbefore defined for formula (V), to give a compound of formula (IIA)

(IIA)

wherein A is as previously defined, followed by deprotection of the amino group to give the compound of formula (II).

Reaction (c). Hydrolysis of the compound of formula (VI);

(VI)

followed by resolution of the resulting enantiomers of a compound of formula (IIR).

For both reactions (a) and (b), the reaction between the compound of formula (IV) and a compound of formulae (V) or (VA) is typically carried out under the Mitsonobu conditions as follows:

Typically, a mixture of the compound of formula (IV) and the compound of formula (V) or formula (VA) in a suitable solvent, such as tetrahydrofuran or toluene, is stirred, suitably for 2-36 hours at a suitable temperature, suitably the reflux temperature of the mixture, under an inert atmosphere, suitably an atmosphere of nitrogen. Further solvent, suitably toluene or tetrahydrofuran, is then added and the mixture cooled, suitably to 0-40° C. A phosphine, suitably triphenyl phosphine, is added and the mixture is stirred. An azodicarboxylate, suitably diisopropylazodicarboxylate, is then added over a period of time, suitably 5-120 min, while maintaining the temperature at <40° C. The mixture is allowed to warm, suitably to 20-40° C. If necessary, further phosphine and azodicarboxylate reagents can be added. After a further period, the reaction mixture is concentrated to near dryness. A suitable alcohol, suitably propan-2-ol or methanol, is added and the concentration step repeated. This may be repeated as necessary. Further alcohol is then added and the mixture may be heated to a temperature suitably 55-75° C. After a suitable period, suitably 20-45 minutes, the resultant slurry is cooled, suitably to 15-25° C., and then allowed to stand, suitably for 1.5-3 hours, after which time the product is isolated by filtration. The filter bed is washed with more alcohol and then dried in vacuo at 35-45° C. to yield the compound of formula (IIAR) or formula (IIA) respectively.

The removal of the protecting group is typically carried out by heating a solution of the compound of formula (IIAR) or formula (IIA) in an appropriate polar solvent, suitably water, in the presence of a mineral acid, suitably concentrated sulfuric acid. The mixture is heated at elevated temperatures, suitably the reflux temperature of the mixture, for a suitable period of time, suitably 8-24 hours. The mixture is then cooled, treated with a suitable apolar solvent, suitably dichloromethane, and treated with a base, suitably 0.88 G aqueous ammonia, maintaining the temperature below 25° C. The aqueous phase is extracted with further apolar solvent, and the combined organic phase is washed with water. The compound of formula (IIR) or (II) is isolated by evaporation to dryness.

The process for the preparation of the compound of formula (IIAR) or formula (IIA) described above may also be undertaken in two stages, in which an intermediate compound of formula (IIBR) or of formula (IIB) respectively;

wherein A is as hereinbefore defined for formulae (V) and (VA); is isolated.

Typically, a mixture of the compound of formula (V) and a compound of formula (V) or formula (VA) in a suitable solvent, such as tetrahydrofuran, C$_{3-4}$ alkanol, toluene, N-methylpyrrolidinone and N,N-dimethylformamide, is stirred, suitably for 2-36 hours at a suitable temperature, suitably the reflux temperature of the mixture under an inert atmosphere, suitably an atmosphere of nitrogen. Further compound of formula (V) is added as necessary and the mixture heated at a suitable temperature, suitably the reflux temperature of the mixture, under an inert atmosphere, suitably an atmosphere of nitrogen, for a suitable period of time. The reaction mixture is then cooled, suitably to 20-25° C., and the compound precipitated by means of addition of a suitable co-solvent, suitably diisopropyl ether. The compound of formula (IIBR) or formula (IIB) respectively is isolated by filtration, washed with further co-solvent and dried in vacuo.

A compound of formula (IIAR) or formula (IIA) may then be prepared from a compound of formula (IIBR) or formula (IIB) respectively using the conditions described for the reaction between the compound of formula (IV) and the compounds of formulae (V) and (VA) hereinbefore described.

Reaction (c) is typically carried out by stirring a solution of the compound of formula (VI) in a suitable solvent, for example a mixture of methanol and water, and adding a suitable base, for example potassium carbonate. The mixture is stirred at a suitable temperature, for example those in the range 20-25° C. for a suitable time, for example 16-20 hours followed by removal of the organic solvent in vacuo. Water is then added and the mixture extracted with a suitable organic solvent, for example ethyl acetate. The combined organic phases are washed with water and saturated aqueous sodium chloride solution before drying over a suitable drying agent, for example sodium sulphate, filtering and evaporation of the solvent in vacuo. The crude product is then purified by flash chromatography.

The resolution of the compound of formula (II) from the racemic product i.e. the compound of formula (IIR) may be undertaken using techniques well known to those skilled in the art, for example preparative chiral high performance liquid chromatography (chiral HPLC) or by fractional crystallisation of diastereoisomeric salts.

The compound of formula (VI) may be prepared by reaction of the compound of formula (VII)

(VII)

with 3,4-dichlorobenzyl chloride.

The reaction between the compound of formula (VII) and 3,4-dichlorobenzyl chloride is typically carried out in a suitable solvent, for example N,N-dimethylformamide, under an inert atmosphere, for example an atmosphere of nitrogen, with the addition of a suitable base, for example potassium carbonate, and a suitable activating agent, such as sodium iodide. The mixture is then stirred at a suitable temperature, for example a temperature in the range of 20-25° C., for a suitable period of time, for example 16-20 hours before removing the volatile components in vacuo.

The compound of formula (VII) is prepared by treating a solution of morpholin-2-ylmethylamine in a suitable organic solvent, for example methanol, under an inert atmosphere, for example an atmosphere of nitrogen, with a solution of ethyl-α,α,α-trifluoroacetate in a suitable anhydrous organic solvent, for example diethyl ether. The mixture is then stirred for a suitable period of time, for example 20-40 minutes at a suitable temperature, for example a temperature in the range of 20-25° C. and the volatile components removed in vacuo. The residue is then dissolved in a suitable organic solvent, for example methanol, and the volatile components removed in vacuo.

It is considered that the compounds of formulae (IIA), (IIBR) and (IIB) are new and form further aspects of the present invention.

The compound of formula (IIR) is known (J. Med. Chem., 1991, 34(2), 616-624).

Morpholin-2-ylmethylamine, ethyl-α,α,α-trifluoroacetate, the compounds of formulae (IV) and (V), and the enantiomers of a compound of formula (V) are known, commercially available compounds, or may be prepared by analogy with known procedures, for examples those disclosed in standard reference texts of synthetic methodology such as *J. March, Advanced Organic Chemistry*, 3rd Edition (1985), Wiley Interscience.

Suitable protecting groups in any of the above mentioned reactions are those used conventionally in the art. The methods of formation and removal of such protecting groups are those conventional methods appropriate to the molecule being protected, for example those methods discussed in standard reference texts of synthetic methodology such as *P J Kocienski, Protecting Groups*, (1994), Thieme.

In any of the above described synthetic procedures, Conventional methods of heating and cooling may be employed, for example electric heating mantles and ice/salt baths respectively. The stability of the compound of the invention may be determined using conventional quantitative analytical methods: For example the stability of the compound in the solid form may be determined by using accelerated stability tests such as differential scanning calorimetry (DSC), thermogravimetric analysis (TGA) and isothermal testing at elevated temperatures including conventional storage tests wherein the test compound is stored under controlled conditions of temperature and humidity over known periods of time. Quantitative analysis of the test compounds, against appropriate reference standards before, during and after the storage period allows the stability of the test compound to be determined. For example, the compound of the invention showed no significant degradation in the following tests: 40° C./20% relative humidity, 25 days; 40° C./75% relative humidity, 25 days; 50° C./ambient conditions, 25 days; light cabinet, ambient conditions, 14 days.

As stated the compound of the invention is more soluble in water than the corresponding free base. Thus a convenient method for determining the stability of the compounds of the invention in aqueous solution involves determining the impurity profiles of an aqueous solution of the test compound at known conditions of temperature and over known periods of time. We have found that the compound of formula (I) shows good aqueous stability in presence and absence of light over 8 days at pH range of 2-10.

The quantitative analysis of the impurity profiles of the compound of the invention in the above mentioned tests may be carried out using conventional methods, generally chromatographic methods such as high performance liquid chromatography (HPLC).

The compound of the invention may be tested for in vitro and in vivo biological activity in accordance with the following assays:

(a) CCR-3 Binding Assay

A CCR-3 competition binding SPA (scintillation proximity assay) was used to assess the affinity of novel compounds for CCR-3. Membranes prepared from K562 cells stably expressing CCR-3 (2.5 μg/well) were mixed with 0.25 mg/well wheat-germ agglutinin SPA beads (Amersham) and incubated in binding buffer (HEPES 50 mM, $CaCl_2$ 1 mM, $MgCl_2$ 5 mM, 0.5% BSA) at 4° C. for 1.5 hr. Following incubation, 20 pM of [$^{125}$I] eotaxin (Amersham) and increasing concentrations of compound (1 pM to 30 μM) were added and incubated in a 96 well plate for 2 hr at 22° C. then counted on a Microbeta plate counter. The total assay volume was 100 μl. Competition binding data were analysed by fitting the data with a four parameter logistic equation. Data are presented as the mean $pIC_{50}$ values (negative logarithm of the concentration of compound which inhibits [$^{125}$I]eotaxin binding by 50%) from at least two experiments.

(b) Eosinophil Chemotaxis Assay.

Compounds were evaluated for their inhibitory effect on eosinophil chemotaxis. Eosinophils were purified from human peripheral blood by standard CD16 cell depletion using a Miltenyi cell separation column and a magnetic Super Macs magnet as previously described (Motegi & Kita, 1998; J. Immunology. 161:4340-6). Cells were re-suspended in RPMI 1640/10% FCS solution and incubated with calcein-AM (Molecular Probes) at 37° C. for 30 mins. Following incubation, the eosinophils were centrifuged at 400 g for 5 min and re-suspended in RPMI/FCS at 2.2 million/ml. Cells were then incubated in the presence of increasing concentration of compounds (1 μM to 30 μM) at 37° C. for 30 mins. For control responses cells were incubated with RPMI/FCS only. The agonist eotaxin (either a concentration response curve or for the functional inhibition curves an $EC_{80}$ concentration) was added to the lower chamber of a 96 well chemotaxis plate (5 μm filter: Receptor Technologies). Eosinophils (50 μl of 2 million/ml cells) were added to the top chamber of the filter plate and incubated at 37° C. for 45 mins. Cells remaining on top of the chemotaxis filter were removed and the number of eosinophils which had migrated were quantified by reading the plate on a fluorescent plate reader. Inhibition curves for the effect of compounds on eosinophil chemotaxis were analysed by fitting the data with a four parameter logistic equation. Functional $pK_i$ values ($fpK_i$) were generated using the equation below (Lazareno & Birdsall, 1995. Br. J. Pharmacol 109: 1110-9).

$$fpKi = \frac{IC_{50}}{1 + \left[\frac{[Agonist]}{EC_{50}}\right]}$$

(c) Guinea-Pig Ovalbumin Model

Inhibition of Eosinophil Infiltration and Hyper-Reactivity in the Guinea Pig

In a method based on that described by Danahay et al., 1997, ovalbumin sensitised guinea pigs were dosed with mepyramine (30 mg $kg^{-1}$, ip) to protect against anaphylactic bronchospasm. Test compounds, dissolved in 10% DMSO and 90% PEG200, were given by the oral route, 30 minutes before ovalbumin challenge (10 minutes breathing of an aerosol generated from a 0.5% solution of ovalbumin). Hyper-reactivity of the airways to the thromboxane mimetic U46619, was measured 24 hours after ovalbumin challenge in un-restrained animals using a whole body plethysmograph (Buxco Ltd., USA). The guinea pigs were then sacrificed and the lungs lavaged. Total and differential leukocyte counts were then obtained for the bronchoalveolar lavage fluid and the percentage reduction in eosinophil accumulation determined (Sanjar et al., 1992). Data were presented as the inhibitory effect of the specified dose expressed as a percentage of the vehicle control response.

Examples of disease states in which the compound of the invention has potentially beneficial anti-inflammatory effects include diseases of the respiratory tract such as bronchitis (including chronic bronchitis), bronchiectasis, asthma (including allergen-induced asthmatic reactions), chronic obstructive pulmonary disease (COPD), cystic fibrosis, sinusitis and rhinitis. Other relevant disease states include diseases of the gastrointestinal tract such as intestinal inflammatory diseases including inflammatory bowel disease (e.g. Crohn's disease or ulcerative colitis) and intestinal inflammatory diseases secondary to radiation exposure or allergen exposure.

Furthermore, the compound of the invention may be used to treat nephritis, skin diseases such as psoriasis, eczema, allergic dermatitis and hypersensitivity reactions and diseases of the central nervous system which have an inflammatory component (e.g. Alzheimer's disease, meningitis, multiple sclerosis) HIV and AIDS dementia.

Compounds of the present invention may also be of use in the treatment of nasal polyposis, conjunctivitis or pruritis.

Further examples of disease states in which the compound of the invention have potentially beneficial effects include cardiovascular conditions such as atherosclerosis, peripheral vascular disease and idiopathic hypereosinophilic syndrome. Other diseases for which the compound of the present invention may be beneficial are other hypereosinophilic diseases such as Churg-strauss syndrome. Additionally, eosinophilia is commonly found in parasitic diseases, especially helminth infections, and thus the compound of the present invention may be useful in treating inflammation arising from hyper-eosinophilic states of diseases such as hydatid cyst (Echinococcus sp.), tapeworm infections (Taenia sp.), blood flukes (schistosomiasis), and nematode (round worms) infections such as:—Hookworm (Ancylostoma sp.), Ascaris, Strongyloides, Trichinella, and particularly lymphatic filariasis including Onchocerca, Brugia, Wucheria (Elephantiasis).

The compound of the invention may be useful as an immunosuppressive agent and so have use in the treatment of autoimmune diseases such as allograft tissue rejection after transplantation, rheumatoid arthritis and diabetes. Compounds of the invention may also be useful in inhibiting metastasis.

Diseases of principal interest include asthma, COPD and inflammatory diseases of the upper respiratory tract involving seasonal and perennial rhinitis.

Preferred diseases of principal interest include asthma and inflammatory diseases of the upper respiratory tract involving seasonal and perennial rhinitis.

Further diseases also of principle interest include inflammatory diseases of the gastrointestinal tract such as inflammatory bowel disease.

It will be appreciated by those skilled in the art that references herein to treatment or therapy extend to prophylaxis as well as the treatment of established conditions.

As mentioned above, the compound of formula (I) is useful as a therapeutic agent There is thus provided as a further aspect of the invention the compound of formula (I) for use as a therapeutic agent, particularly in the treatment of patients with inflammatory conditions, eg. asthma or rhinitis.

According to another aspect of the invention, there is provided the use of the compound of formula (I) for the manufacture of a medicament for the treatment of inflammatory conditions, eg. asthma or rhinitis.

In a further or alternative aspect there is provided a method for the treatment of a human or animal subject suffering from or susceptible to an inflammatory condition eg. asthma or rhinitis, which method comprises administering to said human or animal subject an effective amount of the compound of formula (I).

The compounds according to the invention may be formulated for administration in any convenient way, and the invention therefore also includes within its scope pharmaceutical compositions, comprising the compound of formula (I) optionally with one or more physiologically acceptable diluents or carriers.

There is also provided a process for preparing such a pharmaceutical formulation which comprises mixing the ingredients.

The compound according to the invention may, for example, be formulated for oral, inhaled, intranasal, buccal, parenteral or rectal administration, preferably for oral administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compound may also be formulated as suppositories, e.g. containing conventional suppository bases such as cocoa butter or other glycerides.

The compound according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogenfree water, before use. The dry solid presentation may be prepared by filling a sterile powder aseptically into individual sterile containers or by filling a sterile solution aseptically into each container and freeze-drying.

The compound and pharmaceutical compositions according to the invention may also be used in combination with other therapeutic agents, for example antihistaminic agents, anticholinergic agents, anti-inflammatory agents (such as corticosteroids (e.g. fluticasone prppionate, beclomethasone dipropionate, mometasone furoate, triamcinolone acetonide or budesonide) or NSAIDs (eg. sodium cromoglycate, nedocromil sodium, PDE-4 inhibitors, leukotriene antagonists, iNOS inhibitors, tryptase and elastase inhibitors, beta-2 integrin antagonists and adenosine 2a agonists)) or beta adrenergic agents (such as salmeterol, salbutamol, formoterol, fenoterol or terbutaline and salts thereof), anti-histamines (eg methapyrilene or loratadine) or antiinfective agents (eg. antibiotics, antivirals).

It will be appreciated that when the compound of the present invention is administered in combination with other therapeutic agents normally administered by the inhaled or intranasal route, that the resultant pharmaceutical composition may be administered by the inhaled or intranasal route.

The compound of the invention may conveniently be administered in amounts of, for example, 0.001 to 500 mg/kg body weight, preferably 0.01 to 500 mg/kg body weight, more preferably 0.01 to 100 mg/kg body weight, 1 to 4 times daily. The precise dose will of course depend on the age and condition of the patient and the particular route of administration chosen.

Biological Data

The compound of formula (I) was tested in the CCR-3 binding and/or 40 eosinophil chemotaxis assays (assays (a) and (b)). The compound of the invention tested in the CCR-3 binding assay possessed a pIC50 value of greater than 5. The compound of the invention tested in the CCR-3 eosinophil chemotaxis assay possessed an fpKi value of greater than 5.

Throughout the specification and the claims, unless the context requires otherwise, the word 'comprise', and variations such as 'comprises' and 'comprising', will be understood to imply the inclusion of a stated integer or step or group of integers but not to the exclusion of any other integer or step or group of integers or steps.

The following Examples illustrate the invention but do not limit it in any way.

DETAILED DESCRIPTION

General Experimental Details

NMR

Nuclear magnetic resonance (NMR) spectra were acquired using a Bruker DPX250 or DPX400 instrument.

IR

Infra-red spectra were acquired using a Nicolet Avatar 360 instrument using a Germanium ATR probe LC/MS System A The following Liquid Chromatography Mass Spectroscopy (LCMS) system was used: 3 mm ABZ+PLUS (3.3 cm×4.6 mm internal diameter) column, eluting with solvents: A-0.1% formic acid+0.077% w/v ammonium acetate in water; and B-95:5 acetonitrile:water+0.05% v/v formic acid, at a flow rate of 3 ml per minute. The following gradient profile was used: 100% A for 0.7 min; A+B mixtures, gradient profile 0-100% B over 3.5 min; hold at 100% B for 1.1 min; return to 100% A over 0.2 min.

LC/MS System B 3 μm Phenomenex Luna (50×2 mm i.d.) column, eluting with solvents: A-0.05% trifluoroacetic acid in water, B-0.05% trifluoroacetic acid in acetonitrile, at 40° C. and at a flow rate of 1 ml per minute. The following linear gradient was used: 0 to 95% B over 8 minutes.

Analytical HPLC Column, Conditions and Eluent

Reverse-phase high performance liquid chromatography was carried out using a Luna 3 mm C18(2) (50×2.0 mm i.d.) column eluting with solvents: A-100% water, 0.05% TFA; and B-100% acetonitrile, 0.05% TFA, at a flow rate of 2 ml per minute, and at 60° C. The following gradient profile was used: 0-95% B over 2.00 min, return to 0% B over 0.01 min.

EXAMPLE 1

4-({[({[(2S)-4-(3,4-dichlorobenzyl)morpholin-2-yl] methyl}amino)carbonyl]amino}methyl)benzamide benzenesulfonate dihydrate 4-({[({[(2S)-4-(3,4-dichlorobenzyl)morpholin-2-yl] methyl}amino)carbonyl]amino}-methyl)benzamide (15 g) was suspended in ethanol (60 ml) and water (7.5 ml) at 40° C. A solution of benzene sulfonic acid (6.0 g) in water (7.5 ml) was added, followed by addition of further water (15 ml). Isopropyl acetate (300 ml) was added at 40° C., followed by addition of ethanol (40 ml). The mixture was cooled to 0° C., diluted with cyclohexane (10 ml) and seeded with authentic 4-({[({[(2S)-4-(3,4-dichlorobenzyl)morpholin-2-yl] methyl}amino)carbonyl]amino}methyl) benzamide benzenesulfonate hydrate. The mixture was chilled at 0° C. over 1 h, cyclohexane (100 ml) added over 15 min and the mixture aged at 0° C. The product was isolated by vacuum filtration, washed with isopropyl acetate (2×30 ml) and dried in vacuo at 25±5° to give the title compound as a white solid (16.44 g).

NMR (DMSO d-6): 2.81δ (1H) broad t; 3.0-3.4δ (5H) m; 3.67δ (2H) m; 4.02δ (1H) d of d, J=12.7 Hz, 2.5 Hz; 4.25δ (1H) d, 5.9 Hz; 4.37δ (2H) m; 6.24δ (1H) t, J=5.6 Hz; 6,58δ (1H) t, J=5.9 Hz; 7.3δ (6H) m; 7.48δ (1H) d of d, J=8.3 Hz, 2.0 Hz; 7.61δ (2H) m [benzene sulphonate]; 7.75δ (1H) d, J=8.3 Hz; 7.81δ (1H) d, 2.0 Hz; 7.82δ (2H) m; 7.91δ (1H) broad s; 9.85 (1H) broad s [NH+].

EXAMPLE 2

4-({[({[(2S)-4-(3,4-dichlorobenzyl)morpholin-2-yl] methyl}amino)carbonyl]amino}methyl)benzamide benzenesulfonate dihydrate The slurry of Description 9 was cooled to 50±3° and isopropanol (30 ml) added, followed by an aqueous solution of benzene sulfonic acid (32% w/v, 10 ml). The mixture was cooled to 22±3° over ca 1 h, seeded with authentic 4-({[({[(2S)-4-(3,4-dichlorobenzyl)morpholin-2-yl]methyl}amino) carbonyl]amino}methyl) benzamide hydrate and aged at 22±3° for 72 h. The mixture was cooled to 0±3° over 1 h and filtered. The filter cake was washed with a 4:1:0.1 mixture of isopropyl acetate/isopropyl alcohol/water (2.5 ml) and dried in vacuo at 25±5° to give the title compound as a white solid (6.9 g).

EXAMPLE 3

4-({[({[(2S)-4-(3,4-dichlorobenzyl)morpholin-2-yl] methyl}amino)carbonyl]amino}methyl)benzamide benzenesulfonate dihydrate A solution of 1-[(2S)-4-(3,4-Dichlorobenzyl)morpholin-2-yl]methylamine (60 g) in tetrahydrofuran (120 ml) was added to a suspension of carbonyl diimidazole (38.8 g) in tetrahydrofuran (600 ml) over 25 min at 0-5° C. The mixture was warmed to 10-15° C., and held for 15 min. Isopropanol (30 ml) was added over 10 min, and the mixture was stirred for a further 45 min at 10-15° C. 4-Aminomethyl benzamide (35.9 g) was added, and the mixture was heated to 55-60° C., and held for 90 min. Tetrahydrofuran (240 ml) was removed by distillation, and the mixture was cooled to 20-25° C. The mixture was treated with iso-propyl acetate (480 ml) and 5% aqueous potassium dihydrogen phosphate (480 ml), and the aqueous phase was removed, The organic phase was washed with further 5% aqueous potassium dihydrogen phosphate (2×480 ml), and finally water (480 ml).

The organic phase was concentrated to 250 ml by distillation, diluted with isopropanol (850 ml), and reconcentrated to a final volume of 420 ml. The mixture was cooled to 20-25° C., treated with a solution of benzenesulfonic acid (38.5 g) in water (110 ml) and warmed to 35° C. Isopropyl acetate (720 ml) was added, the mixture was cooled to 20-25° C., and seeded with authentic 4-({[({[(2S)-4-(3,4-dichlorobenzyl) morpholin-2-yl]methyl}amino)carbonyl]amino}-methyl) benzamide benzenesulfonate dihydrate. The mixture was stirred for 3 h at this temperature, treated with further iso-propyl acetate (180 ml), stirred for 30 min and cooled to 0-5° C. The product was isolated by vacuum filtration, washed with isopropyl acetate:isopropanol:water (6:1:0.1, 350 ml) and dried in vacuo at 35±5° to give the title compound as a white solid (115.6 g).

Descriptions

Description 1

2,2,2-Trifluoro-N-(morpholin-2-ylmethyl)acetamide

To a stirred solution of morpholin-2-ylmethylamine (3.1 g) in methanol (70 ml) under nitrogen was added an ethereal solution of ethyl-α,α,α-trifluoroacetate (5 ml in 20 ml ether) which had been washed with saturated aqueous sodium bicarbonate, water and brine, and dried. The mixture was stirred for 30 min at 22° C. before removal of all volatiles in vacuo. The residue was dissolved in methanol (10 ml) and the volatiles again removed in vacuo to give the title compound as a white crunchy foam (4.9 g).

Thermospray Mass Spectrum m/z 213 [MH+].

Description 2

N-{[4-(3,4-Dichlorobenzyl)morpholin-2-yl]methyl}-2,2,2-trifluoroacetamide

To a stirred solution of Description 1 (3.3 g) in N,N-dimethylformamide (50 ml) under nitrogen was added potassium carbonate (2.46 g) and sodium iodide (2.12 g). A solution of 3,4-dichlorobenzyl chloride (2 ml) in N,N-dimethylformamide (10 ml) was added dropwise to the mixture. The mixture was stirred at 22° C. for 18 h before the volatiles were removed in vacuo. The residue was partitioned between dichloromethane (100 ml) and saturated aqueous sodium carbonate solution (50 ml). The organic phase was subsequently washed with additional saturated aqueous sodium carbonate solution (2×50 ml) and water (50 ml) before drying over magnesium sulphate, filtering and evaporation of the solvent in vacuo to give a pale yellow oil. The oil was purified by Biotage flash chromatography on a 90 g silica cartridge eluting with 25% ethyl acetate in cyclohexane, to give the title compound as a colourless oil (2.97 g). LC/MS (System A) $R_t$ 2.63 min, Mass Spectrum m/z 371 [MH$^+$].

Description 3

[4-(3,4-Dichlorobenzyl)morpholin-2-yl]methylamine

To a stirred solution of Description 2 (2.97 g) in methanol (15 ml) and water (5 ml) was added potassium carbonate (5.53 g). The mixture was stirred at 22° C. for 18 h before the methanol was removed in vacuo. Water (25 ml) was added and the mixture extracted with ethyl acetate (3×30 ml). The combined organic phases were washed with water (5 ml) and saturated aqueous sodium chloride solution (10 ml) before drying over sodium sulphate, filtering and evaporation of the solvent in vacuo to give a pale yellow oil. The oil was purified by Biotage flash chromatography on a 90 g silica cartridge eluting with 75:8:1 dichloromethane/ethanol/0.880 ammonia solution. The required fractions were combined and the solvent evaporated in vacuo to give the title compound as a colourless oil (1.85 g).

LC/MS (System A) $R_t$ 1.77 min, Mass Spectrum m/z 275 [MH$^+$].

Description 4

[4-(3,4-Dichlorobenzyl)morpholin-2-yl]methylamine (alternative synthesis)

A mixture of 2-[(3,4-dichlorobenzyl)amino]ethanol (0.980 g) and 2-(oxiran-2-ylmethyl)-1H-isoindole-1,3(2H)-dione (1.10 g) was heated at 80° C. under nitrogen for 3 h. The resulting solid mass was treated with concentrated sulphuric acid (1.5 ml) then stirred at 150° C. for 24 h. The mixture was treated with water (100 ml) then washed with ethyl acetate (2×100 ml). The dark aqueous phase was basified to ~pH 12 using 5M aqueous sodium hydroxide, then extracted with ethyl acetate (2×100 ml). The combined organic extracts were washed with water and brine, dried (Na$_2$SO$_4$) and concentrated under vacuum to give the title compound as a brown oil (1.02 g).

Description 5

1-[(2S)-4-(3,4-Dichlorobenzyl)morpholin-2-yl]methylamine

Description 3 (racemic mixture, 8 g) was separated into its single enantiomers by preparative chiral-HPLC. The separation was carried out using a 2"×22 cm Chiralpak AD 20 μm column, Merck self pack DAC system, eluting with 95:5:0.1 (v/v) heptane: absolute ethanol: diethylamine (flow rate: 55 ml/min over 40 min, UV detection 225 nm); sample load preparation: 400 mg sample in 20 ml 3:2 (v/v) absolute ethanol: system eluent.

The title compound (2.49 g) was obtained as follows: preparative HPLC retention time 23.0 min.

Description 6

1-[(2S)-4-(3,4-Dichlorobenzyl)morpholin-2-yl] methanamine salt with D-tartaric acid 1:1

Description 3 (0.613 g) was dissolved in methanol (12.3 ml). D-Tartaric acid (0.335 g) was added and the slurry was heated to reflux for 50 min. The mixture was allowed to cool to 0-5° C. and the precipitate isolated by filtration to give the title compound as a white solid (0.4 g).

ee: 76% ee Chiral analytical HPLC (Chiralpak AD column, 4.6×250 mm, eluent 50:50:0.1 MeOH: EtOH: Butylamine, flow rate 0.5 ml/min, UV detection at 220 nm), Rt 8.9 min.

Description 7

Preparation of 2-{[(2R)-4-(3,4-dichlorobenzyl)morpholin-2-yl]methyl}-1H-isoindole-1,3(2H)-dione A mixture of 2-[(3,4-dichlorobenzyl)amino]ethanol (2.038 g) and (S)-2-(oxiran-2-ylmethyl)-1H-isoindole-1,3 (2H)-dione (2.032 g) in tetrahydrofuran (3.3 ml) was stirred and heated at reflux under nitrogen. After 21.5 h more tetrahydrofuran (12.5 ml) was added and the mixture was cooled to 3°. Triphenyl phosphine (2.793 g) was added and the mixture was stirred until all the solid had dissolved. Diisopropylazodicarboxylate (2.1 ml) was then added over 12 min maintaining the temperature at <7°. After 2.25 h the mixture was allowed to warm to 22°. After 5.3 h more triphenylphosphine (121 mg) and diisopropylazodicarboxylate (0.09 ml) were added. After 22.5 h the reaction mixture was concentrated to near dryness. Propan-2-ol (12 ml) was added and the concentration repeated, this was repeated once more. More propan-2-ol (12 ml) was added and the mixture was heated to 70°. After 0.5 h the slurry was cooled to 22° and then after a further 2 h the product was collected. The bed was washed with propan-2-ol (2×4 ml) and then dried in vacuo at 40° to give the title compound (2.622 g).

NMR (DMSO d-6): 1.93δ (1H) d of d, J=11.0 Hz, 8.8 Hz; 2.10δ (1H) d of t, J=3.5 Hz, 11.3 Hz; 2.52δ (1H) broad d, J=11.3 Hz; 2.77δ (1H) broad d, J=11.3 Hz; 3.3-3.8δ (7H) m; 7.31δ (1H) d of d, J=8.2 Hz, 1.9 Hz; 7.55δ (1H) d, J=1.9 Hz; 7.68δ (1H) d, J=8.2 Hz; 7.86δ (4H) m.

Description 8

Preparation of [(2S)-4-(3,4-dichlorobenzyl)morpholin-2-yl]methylamine

A slurry of Description 7 (1.00 g) in water (8.5 ml) was heated to 75° and then treated dropwise with concentrated sulphuric acid (2.5 ml). The mixture was then heated at reflux. After 23 h the reaction mixture was cooled to 22° and then treated with dichloromethane (6 ml). 880 Ammonia solution (7 ml) was then added dropwise with cooling. More dichloromethane (10 ml) was added. The aqueous phase was separated and extracted with more dichloromethane (10 ml). The combined organic phase was washed with water (5 ml) and then evaporated to dryness. The residue was reevaporated from DCM to give the title compound as an oil (662 mg).

NMR (DMSO d-6): 1.78δ (1H) t, J=10.5 Hz; 2.06δ (1H) d of t, J=3.4 Hz, 11.3 Hz; 2.45-2.65δ (3H) m; 2.73δ (1H) d of t, J=11.3 Hz, 1.7 Hz; 3.38δ (1H) m; 3.46δ (2H) AB q; 3.51δ

(1H) d of d, J=11.3 Hz, 2.5 Hz; 3.77δ (1H) d of m, J=11.3 Hz; 7.31δ (1H) d of d, J=8.3 Hz, 2.0 Hz; 7.55δ (1H) d, J=2.0 Hz; 7.58δ (1H) d, J=8.3 Hz.

Description 9

4-({[({[(2S)-4-(3,4-ichlorobenzyl)morpholin-2-yl] methyl}amino)carbonyl]amino}methyl)benzamide A solution of (5 g) in THF (10 ml) was added to a slurry of N,N'-carbonyldiimidazole (3.2 g) in THF (30 ml) at 5-10° C. over ca. 10 min. The mixture was warmed to 15±3° and held at this temperature for ca. 15 min. 4-Aminomethyl benzamide (3.0 g) was then added, the mixture heated to 60+3° and stirred at this temp for 75 min.

The reaction was cooled to 22±3° and isopropyl acetate (40 ml) added, followed by a solution of potassium dihydrogen phosphate (5% w/v, 40 ml). The solution was filtered through celite (2 g), the lower aqueous layer was removed and the upper organic layer washed with potassium dihydrogen phosphate (5% w/v, 2×40 ml) then water (40 ml). The organic phase was distilled at atmospheric pressure to remove THF and leave a slurry of 4-({[({[(2S)-4-(3,4-dichlorobenzyl) morpholin-2-yl]methyl}amino)carbonyl]amino}methyl) benzamide in isopropyl acetate (ca 60 ml).

The slurry containing 4-({[({[(2S)-4-(3,4-dichlorobenzyl) morpholin-2-yl]methyl}amino)carbonyl]amino}methyl) benzamide may be used directly for the process of Example 2, or filtered to give 4-({[({[(2S)-4-(3,4-dichlorobenzyl)morpholin-2-yl]methyl}amino)carbonyl]amino}methyl)benzamide in isolated form for use in the process of Example 1.

Description 10

2-{(2R)-3-[(3,4-dichlorobenzyl)(2-hydroxyethyl) amino]-2-hydroxypropyl}-1H-isoindole-1,3(2H)-dione To a solution of 2-[3,4-dichlorobenzyl)amino]ethanol (2.8 g) in tetrahydrofuran (6.2 ml) is added (S)-2-(oxiran-2-ylmethyl)-1H-isoindole-1,3(2H)-dione (3.1 g) with stirring, under a nitrogen atmosphere. The mixture was heated to 90° C. over 1 h, then held at this temperature for 18 h. Further 2-[3,4-dichlorobenzyl)amino]ethanol (0.14 g) is added, and the reaction mixture heated to 90° C. for a further 5 h. The reaction mixture is cooled to 22° C., and diisopropyl ether (21 ml) added, and the product isolated by vacuum filtration. The filter cake is washed with diisopropyl ether (3 ml) and dried in vacuo at 40° to give the title compound as a white solid (4.79 g).

LC/MS (System B) $R_t$ 3.85 min, Mass Spectrum m/z 423 [MH$^+$]

Description 11

Preparation of [(2S)-4-(3,4-dichlorobenzyl)morpholin-2-yl]methylamine (alternative deprotection)

A slurry of Description 7 (70.00 g) in 40% w/w aqueous methylamine (560 ml) was heated to 50-600 and held for 3 h. The mixture was treated dropwise with 10N sodium hydroxide (35 ml), cooled to <25° and then treated with dichloromethane (210 ml). The aqueous phase was separated and extracted with more dichloromethane (210 ml). The combined organic phase was washed with water (70 ml) and then evaporated to dryness. The residue was reevaporated from DCM to give the title compound as an oil (47.7 g).

Description 12

4-({[({[(2S)-4-(3,4-dichlorobenzyl)morpholin-2-yl] methyl}amino)carbonyl]amino}methyl)benzamide A mixture of [(2S)-4-(3,4-dichlorobenzyl)morpholin-2-yl]methylamine, 1:1 salt with D-tartaric acid (20 g), water (100 ml) and dichloromethane (120 ml) was treated with aqueous ammonia (10 ml) at 15-25° C. The layers were separated, the aqueous layer was washed with dichloromethane (30 ml) and the combined organic layers were washed with 2% aqeous sodium chloride (20 ml). The organic phase was concentrated to an oil, and taken up in THF (20 ml). This solution was added to a slurry of N,N'-carbonyldiimidazole (7.8 g) in THF (80 ml) at 0-5° C. over ca. 10 min. The mixture was warmed to 15±3° and held at this temperature for ca. 15 min. Isopropanol (6 ml) was added, and stirred for a further 5 min at 15±3°. 4-Aminomethyl benzamide (7.2 g) was then added, the mixture heated to 60±3° and stirred at this temp for 120 min.

The reaction was cooled to 22±3° and isopropyl acetate (96 ml) added, followed by a solution of potassium dihydrogen phosphate (5% w/v, 96 ml). The organic phase was washed with further potassium dihydrogen phosphate (5% w/v, 2×96 ml), and then water (96 ml). The organic phase was filtered through Celite, and the cake was washed with isopropyl acetate. The filtrate was concentrated to a semi-solid and resuspended in isopropyl acetate (200 ml) at reflux. The slurry was cooled to 20-25° C. over 1 h, cooled to 0-5° C. and aged for 15 min. The product was isolated by filtration, washed with isopropyl acetate (50 ml) and dried in vacuo to give the title compound as a white solid (17.4 g).

LC-MS (System A) $R_t$ 2.27 min, Mass Spectrum m/z 451/ 453 (MH+)

Description 13

Preparation of 2-{[(2R)-4-(3,4-dichlorobenzyl)morpholin-2-yl]methyl}-1H-isoindole-1,3(2H)-dione A mixture of 2-[(3,4-dichlorobenzyl)amino]ethanol (400 g) and (S)-2-(oxiran-2-ylmethyl)-1H-isoindole-1,3(2H)-dione (399.6 g) in toluene (1150 ml) was stirred and heated at 103-107° C. under nitrogen. After 22.5 h the mixture was cooled to <60° C. and charged with tetrahydrofuran (2800 ml). Triphenyl phosphine (548 g) was added and the mixture was stirred until all the solid had dissolved, then cooled to 5-9° C. Diisopropylazodicarboxylate (412 ml) was then added over 70 min maintaining the temperature at <12°. The mixture was warmed to 21-25° and stirred for 1.5 h. The reaction mixture was concentrated by distillation to a final volume of 2800 ml. Methanol (2800 ml) was added and the concentration repeated to a volume of 2800 ml. More methanol (2000 ml) was added and the mixture was heated to 55°. After 0.75 h the slurry was cooled to 18° and then after a further 1 h the product was collected. The bed was washed with methanol (2×1200 ml) and then dried in vacuo at 40° to give the title compound (526.9 g).

X-ray Diffraction

Figure 1:
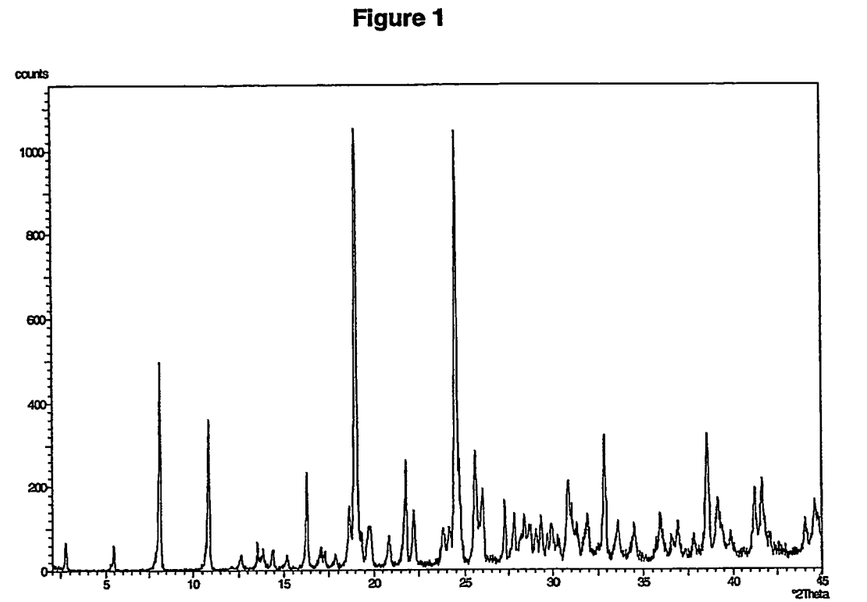
FIG. 1 is an X-ray diffraction pattern for a compound of formula (I) dihydrate.

X-ray diffraction data for (4-({[({[(2S)-4-(3,4-dichlorobenzyl)morpholin-2-yl]methyl}amino)carbonyl] amino}methyl)benzamide benzenesulfonate dihydrate is shown in FIG. 1. Table 1 below sets out the instrument and parameters used. Table 2 below sets out the peak listings.

TABLE 1

Instrument and instrument parameters used for data collection

| | |
|---|---|
| Manufacturer | Philips Analytical X-Ray B.V. The Netherlands |
| Diffractometer Type | PW3040 |
| Serial | DY667 |
| Tube Anode | Cu |
| K-Alpha1 wavelength (Å) | 1.54056 |
| K-Alpha2 wavelength (Å) | 1.54439 |
| RatioAlpha2:1 | 0.50000 |
| Divergence Slit | Prog. Div. Slit |
| Receiving Slit | Prog. Rec. Slit |
| Monochromator Used | YES |
| Generator Voltage (kV) | 40 |
| Tube Current (mA) | 55 |
| File Date &Time | 6-Feb-2002 16:41 |
| Data Angle Range (°2Θ) | 6.0000-45.0000 |
| Scan Step Size (°2Θ) | 0.020 |
| Scan Type | CONTINUOUS |
| Scan Step Time | 1.00 |

TABLE 2

Peak listings

| Angle (°2Θ) | Relative Intensity (%) |
|---|---|
| 2.76106 | 5.94 |
| 5.46331 | 4.86 |
| 8.15276 | 46.78 |
| 10.86567 | 32.69 |
| 12.65525 | 3.49 |
| 13.56421 | 4.50 |
| 13.86964 | 4.02 |
| 14.42106 | 4.40 |
| 15.16974 | 3.27 |
| 16.30551 | 20.75 |
| 17.00973 | 3.59 |
| 17.25384 | 3.43 |
| 17.86169 | 3.06 |
| 18.60297 | 11.16 |
| 19.03017 | 100.00 |
| 19.31215 | 8.30 |
| 19.78254 | 9.12 |
| 20.81643 | 7.56 |
| 21.78742 | 17.42 |
| 22.21255 | 13.05 |
| 23.77012 | 8.99 |
| 24.12210 | 9.17 |
| 24.51820 | 98.77 |
| 25.60615 | 26.57 |
| 26.02674 | 18.28 |
| 27.29165 | 15.60 |
| 27.84695 | 11.08 |
| 28.40132 | 12.40 |
| 28.77836 | 8.06 |
| 29.06108 | 9.05 |
| 29.34410 | 11.99 |
| 29.70510 | 7.17 |
| 29.92808 | 9.79 |
| 30.32458 | 6.73 |
| 30.85363 | 19.87 |
| 31.34853 | 9.33 |
| 31.92524 | 12.43 |
| 32.87292 | 29.68 |
| 33.64329 | 9.79 |
| 34.51241 | 10.24 |
| 35.94723 | 12.27 |
| 36.60514 | 7.34 |
| 36.92942 | 10.80 |
| 37.79933 | 7.29 |
| 38.57353 | 28.83 |
| 39.13941 | 16.12 |
| 39.88994 | 7.27 |
| 41.25329 | 18.40 |
| 41.68381 | 19.20 |
| 42.10577 | 6.85 |
| 43.99694 | 10.82 |
| 44.55330 | 14.98 |

Differential Scanning Calorimetry

Figure 2:
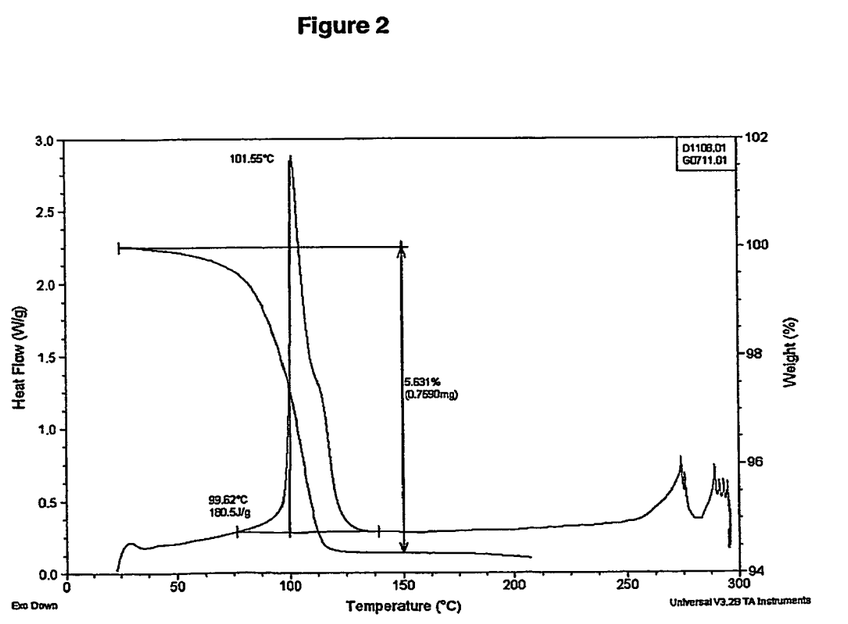
FIG. 2 is a combined Thermogravimetric Analysis/Differential Scanning Calorimetry trace for a compound of formula (I) dihydrate.
Figure 3:
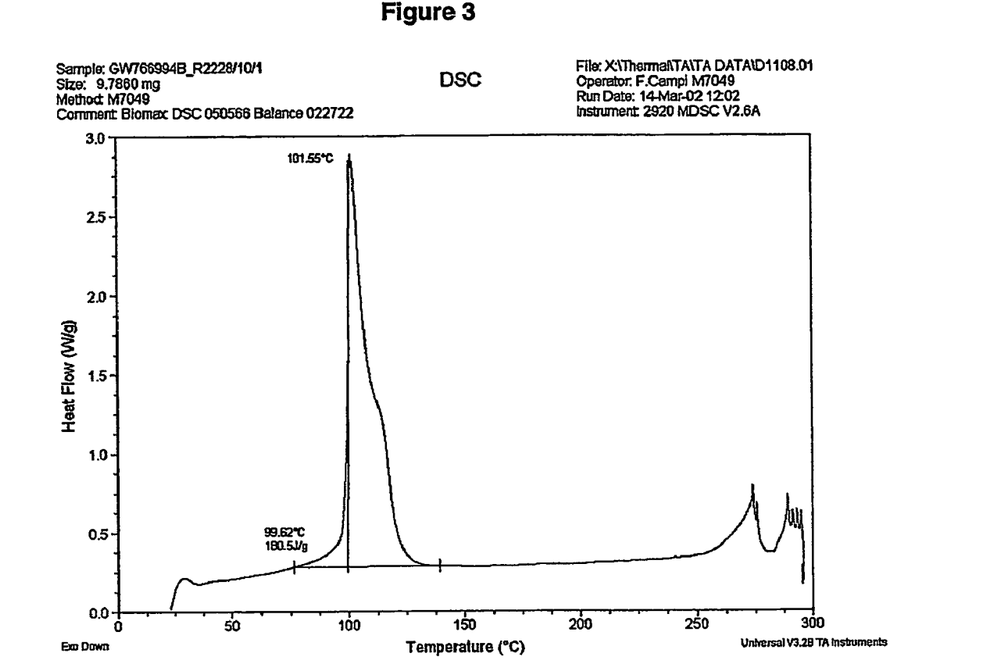
FIG. 3 is a Differential Scanning Calorimetry trace for a compound of formula (I) dihydrate.

The stability of 4-({[({[(2S)-4-(3,4-dichlorobenzyl)morpholin-2-yl]methyl}amino)carbonyl]amino}methyl)benzamide benzenesulfonate dihydrate was measured using differential scanning calorimetry. Table 3 sets out the instrument and parameters used and the results are shown in FIGS. 2 and 3.

TABLE 3

| | | |
|---|---|---|
| Instrument | Manufacturer/ Model: | TA Instruments DSC2920 |
| | Serial No. | M2920-234 |
| Method | Sample pre-treatment | None |
| | Purge gas identity/ flow rate | Nitrogen/20 ml min$^{-1}$ |
| | Sample pan type | Pinhole aluminium |
| | Heating rate | 10° C. min$^{-1}$ |
| | Temperature range | Ambient to 300° C. |

Thermogravimetric Analysis

Figure 4:
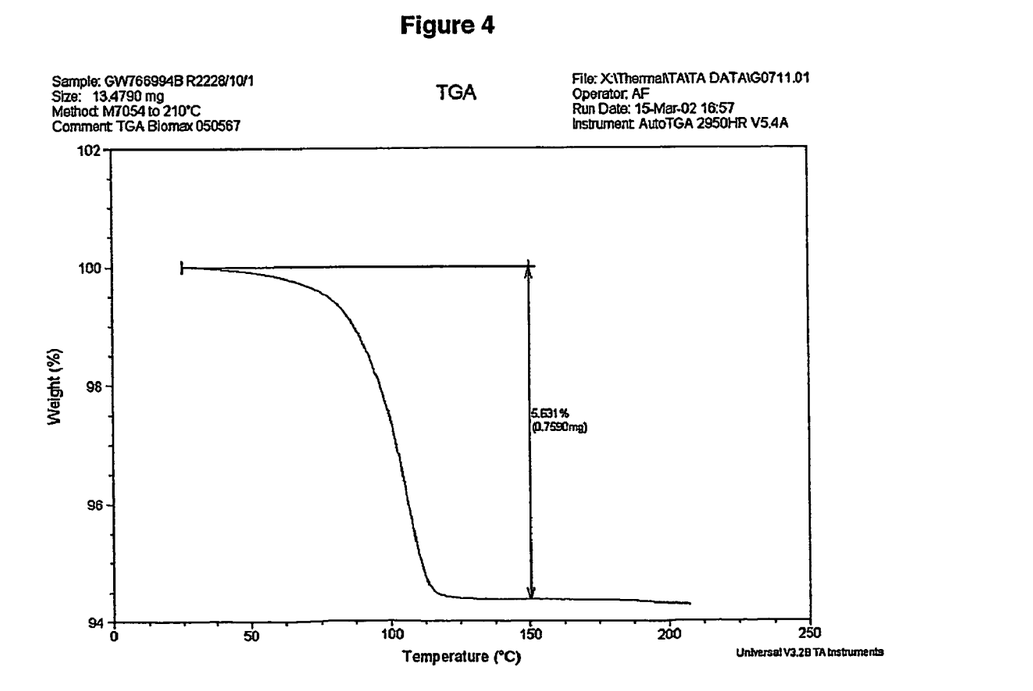
FIG. 4 is a Thermogravimetric Analysis trace for a compound of formula (I) dihydrate.

The stability of 4-({[({[(2S)-4-(3,4-dichlorobenzyl)morpholin-2-yl]methyl}amino)carbonyl]amino}methyl)benzamide benzenesulfonate dihydrate was measured using thermogravimetric Analysis. Table 4 sets out the instrument and parameters used and the results are shown in FIG. 4.

TABLE 4

| | | |
|---|---|---|
| Instrument | Manufacturer/ Model: | TA Instruments TGA2950 |
| | Serial No. | HA29250-226 |
| Method | Sample pre-treatment | None |
| | Purge gas identity/ flow rate | Nitrogen/100 ml min$^{-1}$ |
| | Sample pan type | Open aluminium |
| | Heating rate | 10° C. min$^{-1}$ |
| | Temperature range | Ambient to 300° C. |

The invention claimed is:

1. A compound of formula (I):

wherein A⁻ is the benzenesulphonate (besylate) anion;
R is H or $C_{1-6}$ alkyl; and
n is a number from 0.8 to 2.2.

2. A compound of formula (I) according to claim 1 wherein R is H.

3. A compound of formula (I) according to claim 1 wherein n is a number between 1.1 and 2.1.

4. A compound of formula (I) according to claim 1 wherein n is 2.

5. A compound according to claim 1 which is 4-({[({[(2S)-4-(3,4-dichlorobenzyl)morpholin-2-yl]methyl}amino)carbonyl]amino} methyl)benzamide benzenesulfonate dihydrate.

6. A process for the preparation of a compound of formula (I) as defined in claim 1, which process comprises the reaction of a compound of formula (IA);

with a source of the besylate anion and a suitable $C_{1-6}$alkanol and water.

7. A compound of formula (I) as defined in claim 1 for use as a therapeutic agent in the treatment of patients with inflammatory conditions.

8. A method of manufacture of a medicament comprising the step of incorporating a compound of formula (I) as defined in claim 1 in a pharmaceutical composition.

9. A method for the treatment of a human or animal subject suffering from an inflammatory condition comprising rhinitis and/or asthma, which method comprises administering to said human or animal subject an effective amount of a compound of formula (I) as defined in claim 1.

10. A pharmaceutical composition, comprising a compound of formula (I) as defined in claim 1 optionally with one or more physiologically acceptable diluents or carriers.

11. The method of treatment of claim 9, wherein the inflammatory condition is asthma.

12. The method of treatment of claim 9, wherein the inflammatory condition is rhinitis.

* * * * *

UNITED STATES PATENT AND TRADEMARK OFFICE
CERTIFICATE OF CORRECTION

PATENT NO. : 7,531,651 B2  Page 1 of 1
APPLICATION NO. : 10/509521
DATED : May 12, 2009
INVENTOR(S) : Cook et al.

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by 600 days Delete the phrase "by 600 days" and insert -- by 1006 days --

Signed and Sealed this

Twentieth Day of April, 2010

David J. Kappos
*Director of the United States Patent and Trademark Office*